United States Patent [19]
Kenyon et al.

[11] Patent Number: 5,342,362
[45] Date of Patent: Aug. 30, 1994

[54] SYSTEM AND INSTRUMENTATION FOR TORSIONALLY TESTING FEMORAL RASP AND HIP STEM IMPLANT INCLUDING MOTION INDICATOR

[75] Inventors: Roger R. Kenyon; Mark D. Landes; Donna L. Campana, all of Warsaw; Perry A. Geremakis, South Bend; Ted L. Dock; Jeffrey M. Ondrla, both of Warsaw, all of Ind.

[73] Assignee: Zimmer Inc., Warsaw, Ind.

[21] Appl. No.: 751,907

[22] Filed: Aug. 29, 1991

[51] Int. Cl.5 ............................................. A61B 17/00
[52] U.S. Cl. ........................................ 606/79; 606/85
[58] Field of Search ............... 606/79, 80, 83, 84, 606/85; 623/16, 18, 20, 22, 23, 66

[56] References Cited

U.S. PATENT DOCUMENTS

| | | | |
|---|---|---|---|
| 4,601,289 | 7/1986 | Chiarizzio | 606/85 |
| 4,728,334 | 3/1988 | Spotorno | 623/23 |
| 4,765,328 | 8/1988 | Keller | 606/85 |
| 4,770,660 | 9/1988 | Averill | 623/23 |
| 4,921,493 | 5/1990 | Webb | 606/85 |
| 4,922,898 | 5/1990 | Dunn | 623/16 |
| 4,963,155 | 10/1990 | Lazzeri | 606/85 |
| 5,002,581 | 3/1991 | Paxson | 623/18 |

*Primary Examiner*—Michael A. Brown
*Attorney, Agent, or Firm*—Todd A. Dawson

[57] ABSTRACT

The system and instrumentation of this invention provides a torque wrench adapter for the femoral rasp and for the hip stem implant. Each adapter includes a shaft for connecting a motion indicator thereon. The motion indicator includes a port for accepting the shaft of either the rasp adapter or the implant adapter and an indicator needle which is linked through spring mechanisms to shiftable leg. In use, the leg is anchored at one end to the femur such that the leg moves with the femur and relative to the indicator housing which causes a deflection in the indicator needle to apprise the surgeon of small movement of either the rasp or the implant relative to the femur.

6 Claims, 7 Drawing Sheets

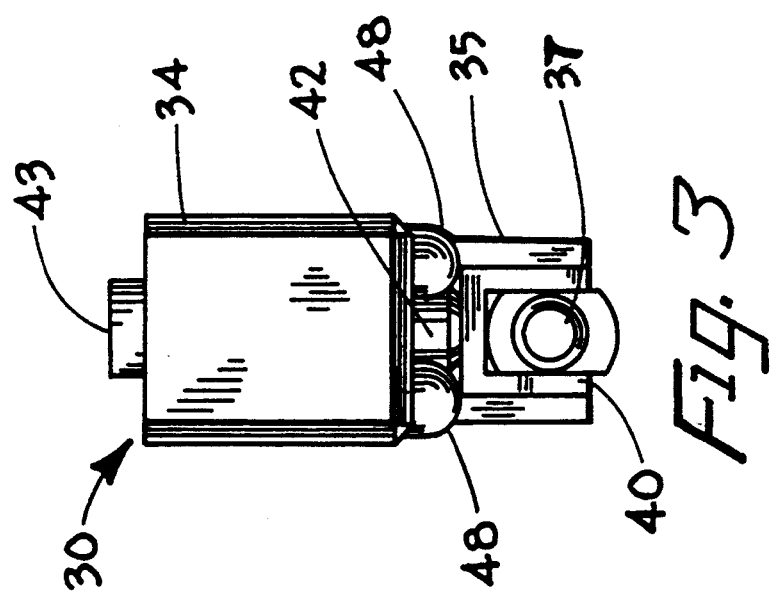
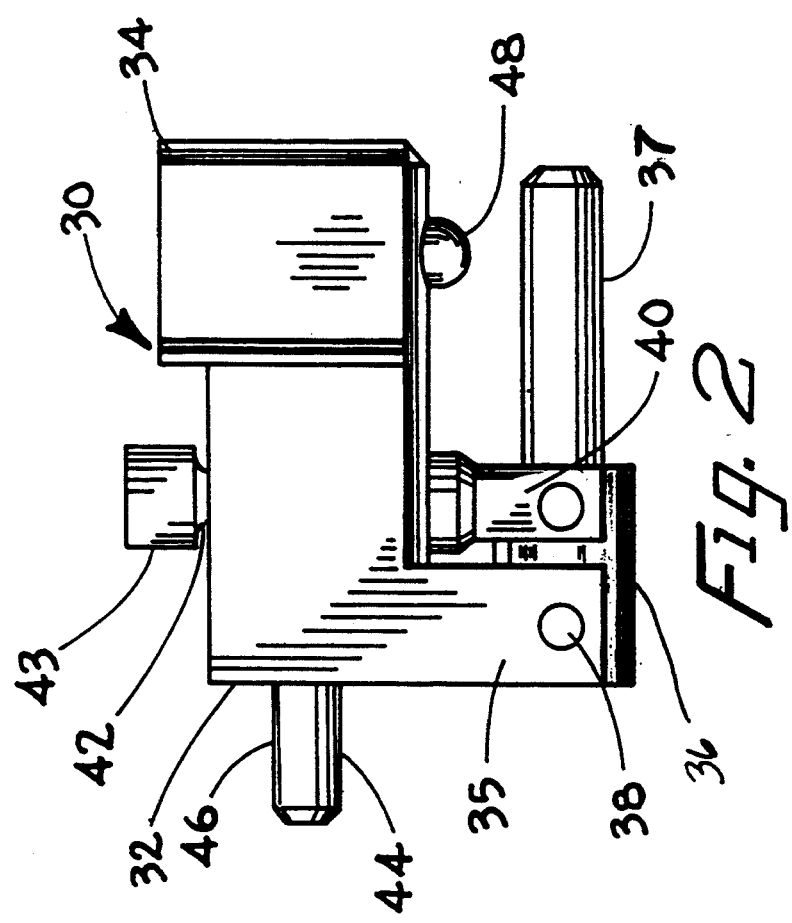

SYSTEM AND INSTRUMENTATION FOR TORSIONALLY TESTING FEMORAL RASP AND HIP STEM IMPLANT INCLUDING MOTION INDICATOR

FIELD OF THE INVENTION

This invention relates to a system and to the instrumentation for torsionally testing the fit between a femoral rasp and a medullary canal and a hip stem implant and a medullary canal. The system and instrumentation including a motion indicator for visually indicating movement between either the rasp or implant relative to the medullary canal.

BACKGROUND OF THE INVENTION

It has become well accepted, if not universally accepted, that to ensure a proper seating of a hip stem implant and to reduce failure rates at the bone/prosthesis junction the prosthesis when seated should withstand a predetermined amount of torque without significant movement relative to the femur. Typically, this type of testing is accomplished by connecting a torque wrench to the rasp handle or implant. If visual movement between the rasp or prosthesis and femur is not observed by the surgeon when torque of approximately 180 inch pounds is applied, it is believed that the medullary canal of the femur is properly prepared for accommodating the appropriate size of hip stem implant. A more thorough explanation of the necessity of torsional testing of a rasp and hip stem implant may be had by reference to U.S. Pat. No. 4,922,898 issued to Dunn and incorporated herein by reference.

A prosthetic hip stem implant with a torque adapter designed to connect a torque wrench to the implant without marring the finish of the implant is illustrated and described in U.S. patent application Ser. No. 603,338 filed on Nov. 5, 1990 and incorporated herein by reference.

The torque adapters and method of the above identified patent and application for patent, rely on the surgeon to closely monitor the bone/prosthesis junction to determine if movement occurs while torque force is applied to the implant.

SUMMARY OF THE INVENTION

The system and instrumentation of this invention provides a torque wrench adapter for the femoral rasp and for the hip stem implant. Each adapter includes a shaft for connecting a motion indicator thereon. The motion indicator which has a port for accepting the shaft of either the rasp adapter or the implant adapter includes indicia thereon and an indicator needle which is linked through spring mechanisms to an indicator arm. In use, the indicator arm is anchored to the femur such that movement of the indicator relative to the femur causes a deflection in the indicator needle to apprise the surgeon of small movement of either the rasp or the implant relative to the femur. Therefore, the micro-motion indicator in association with the rasp torque adapter and implant torque adapter detects and visually indicates minute movement between the rasp or implant and the femur. Such minute movement may otherwise be difficult to detect visually and could go unnoticed.

The method of using the instrumentation of this invention calls for the rasp to be seated into the intramedullary canal after substantial rasping of the canal has been performed including calcar preparation. The rasp torque adapter of the invention is connected to the exposed end of the rasp and the motion indicator is securely connected to a shaft extending outwardly of the rasp adapter. The indicator arm is clamped to a pin driven into the femur to secure the distal end of the indicator arm against movement. A torque wrench is connected to the rasp torque adapter and torque is applied to the rasp and rasp adapter. If relative movement occurs between the rasp and femur during torquing of the rasp, the motion indicator arm is pivoted about its anchor point thereby causing a deflection in the indicator needle. If no movement has occurred or the surgeon determines that the movement under torque is plastic and not static, the rasp is removed and the implant is seated into the prepared intramedullary canal. If the movement is considered by the surgeon to be significant, rasping and torsional testing of the canal continues until the surgeon determines the canal is properly prepared for the implant.

During a revision procedure, a torque wrench adapter is connected to the hip stem implant. The motion indicator is connected to the implant torque adapter in a similar manner as with the rasp torque adapter and again anchored to the femur. Torque is applied to the implant through the adapter and again the surgeon watches the indicator for a deflection. A deflection in the indicator needle indicates relative movement between the bone and implant. It is the surgeon's decision whether such movement is to be considered significant requiring further canal modification or a different implant.

Accordingly, it is an object of the invention to provide a novel system for torsionally testing the fit or stability between a rasp or implant and a prepared medullary canal of a femur.

Another object of the invention is to provide for a motion indicator for connection to a torque adapter for indicating relative movement between an implant or rasp and the prepared medullary canal of a femur.

Another object of the invention is to provide for a torque wrench adapter for a femoral rasp including a shaft for connection to a motion indicator.

Another object of the invention is to provide for a torque wrench adapter for a hip stem implant including a shaft for connection of a motion indicator.

Yet another object of the invention is to provide for a method of indicating motion between an implant or rasp and the prepared medullary canal of a femur.

Still other objects of the invention will become apparent upon a reading of the following description taken with the accompanying drawings.

BRIEF DESCRIPTION OF THE DRAWINGS

FIG. 2 is a side elevational view of the implant torque wrench adapter of the invention.

FIG. 3 is an end view of FIG. 2.

DESCRIPTION OF THE PREFERRED EMBODIMENTS

The preferred embodiments herein disclosed are not intended to be exhaustive or to limit the invention to the precise forms disclosed. Rather, they are chosen and described in order to best explain the invention so that others skilled in the art might utilize their teachings.

Figure 1:
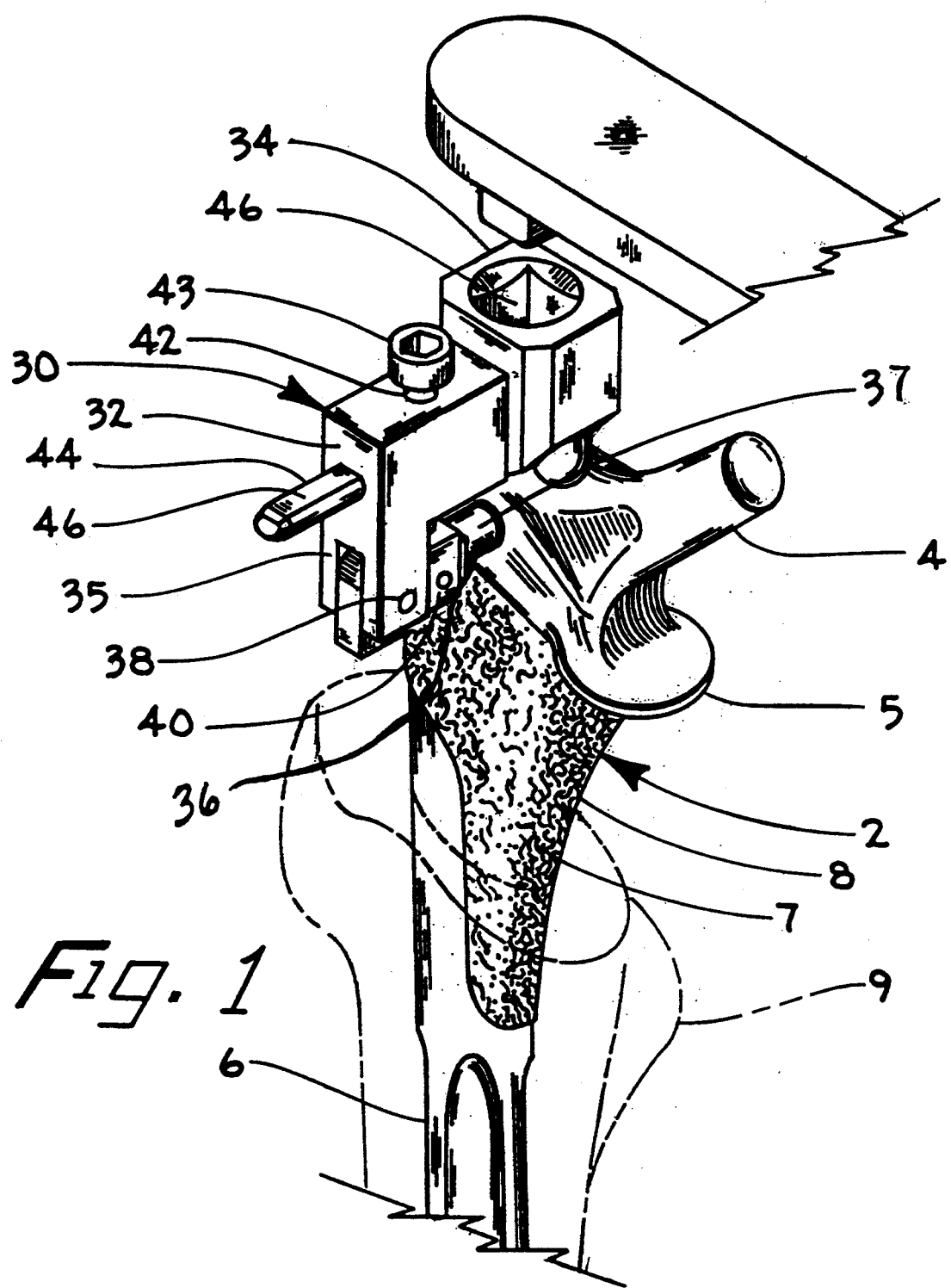
FIG. 1. is a perspective view of a hip stem implant partially seated within an medullary canal of a femur's proximal end (shown in broken lines) with the torque wrench adapter connected thereto. A torque wrench is partially shown for illustrative purposes only.
Figure 11:
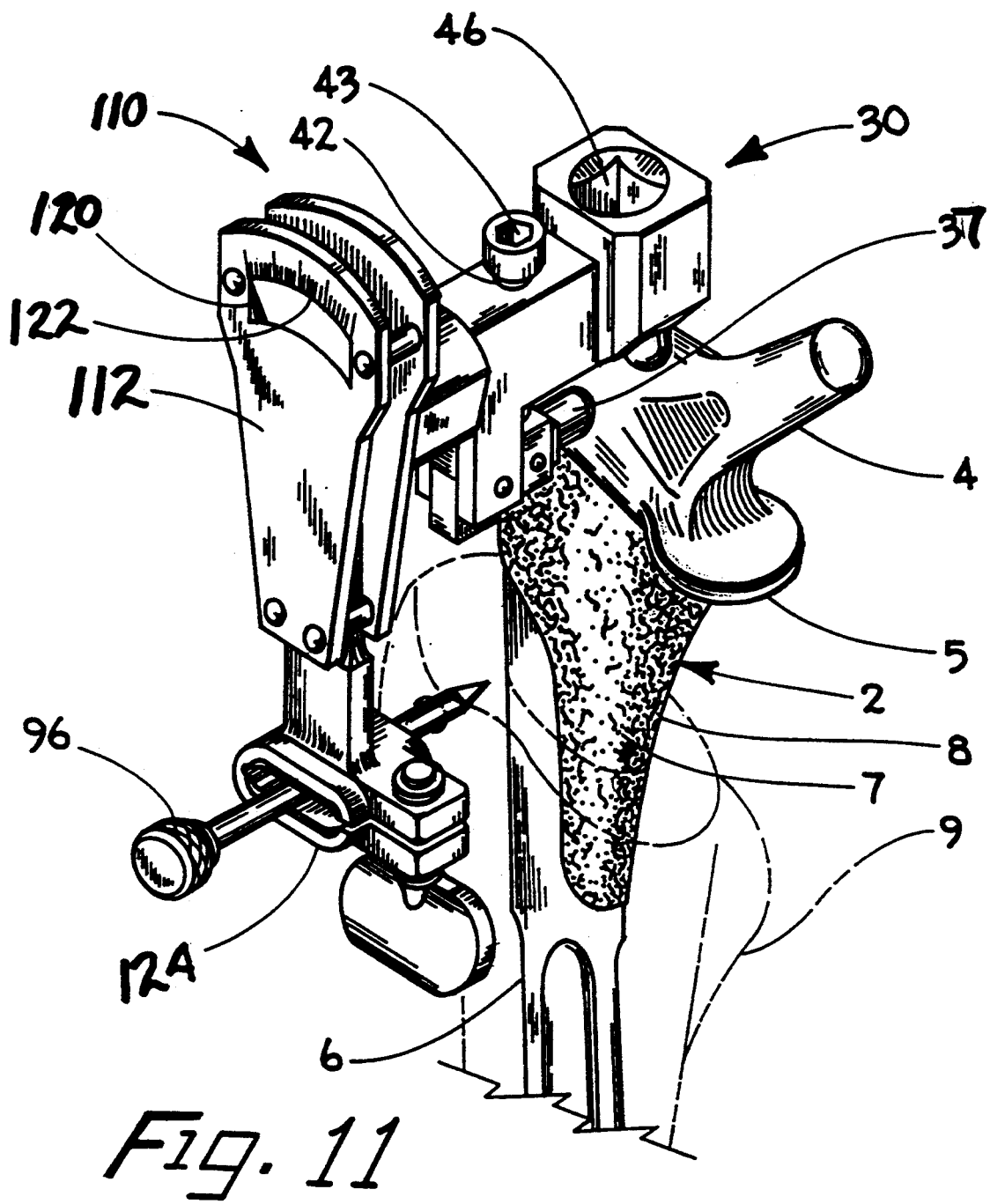
FIG. 11 is a perspective view of the implant torque wrench adapter connected to hip stem implant. A motion indicator is secured to the torque adapter and anchored to the femur (shown in broken lines only).

A prosthetic hip stem implant 2 is illustrated in FIGS. 1 and 11 for illustrative purposes only and includes neck 4 and a fluted stem 6 joined by a body 8 at their junction. Neck 4 is adapted to accommodate a prosthetic hip ball (not shown). Stem 6 is adapted for insertion into the intramedullary canal of a femur 9 shown in broken lines. A fiber metal porous surface layer 7 is carried by the implant 2 on body 8. A lip or collar 5 extends from body 8. An extraction bore extends through body 8. A punch recess having an arcuate bottom is formed in the upper surface of body 8 and defines a striking point for impacting the implant into the medullary canal of the femur. A pair of recesses are formed on the upper surface of the body 8 on opposite sides of punch recess. A more thorough understanding of the hip stem may be had by reference to U.S. patent application Ser. No. 603,338 filed on Nov. 5, 1990 previously incorporated by reference.

Adapter 30 includes a generally L-shaped housing 32 having a head 34 as an integral part. Head 34 includes an interior squared socket 46 and a pair of lower extending nipples 48. An arm 36 is pivotally or movable connected to the lower extending leg 35 of housing 32 by a pivot pin 38. Arm 36 includes a cylindrical portion 37. A bracket 40 is connected to arm 36 between leg 35 of housing 32 and the cylindrical portion 37 of the arm. An adjustment screw 42 extends through housing 32 and is threaded into bracket 40. Adjustment screw 42 includes a common hex head socket 43 which extends above housing 32. In the alternative, the adjustment screw 42 could move the arm 36 and cylindrical portion 37 up and down relative to a slot formed in the leg 35 for receiving the end of arm 36. As thus far described adapter 30 is substantially similar to the adapter as illustrated and described in the incorporated application. A thorough understanding of the operation of the adapter may be had by reference to the incorporated application. Body 30 further includes, an arm 44 extends outwardly from housing 32 in an opposite direction from arm 36. Arm 44 includes a flattened portion 46 as is best illustrated in FIG. 1.

Figure 4:
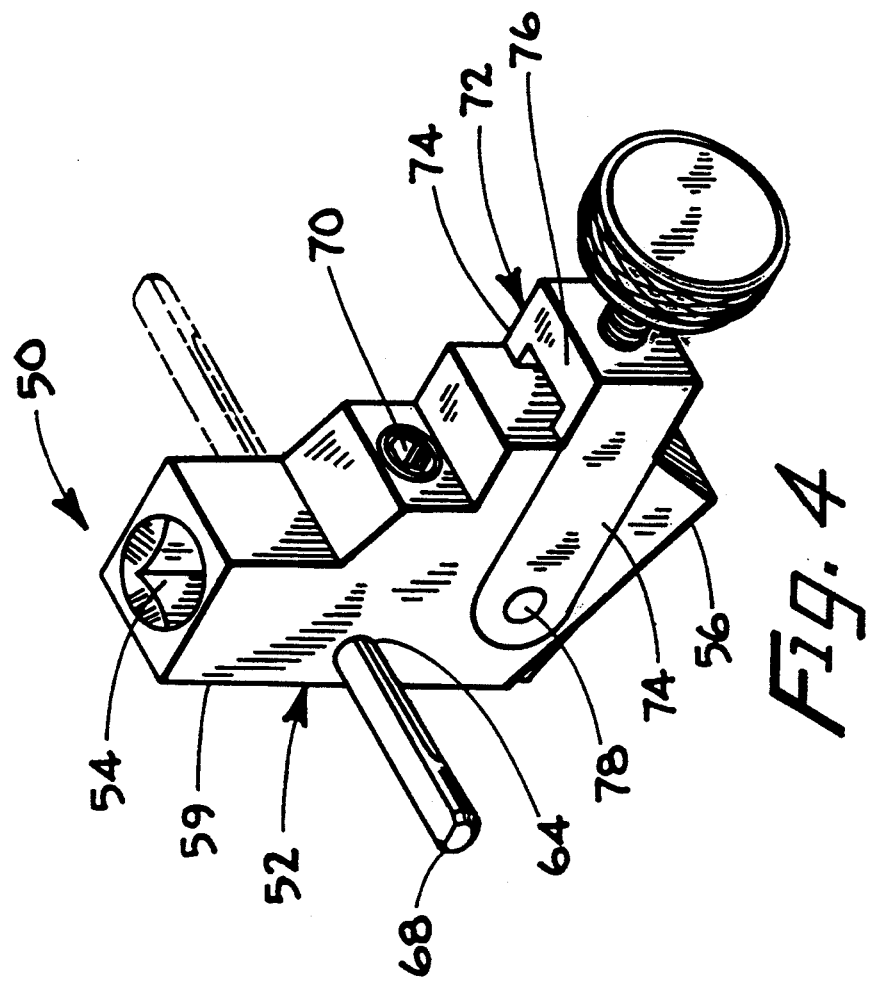
FIG. 4 is a perspective view of the torque wrench adapter for a rasp.
Figure 7:
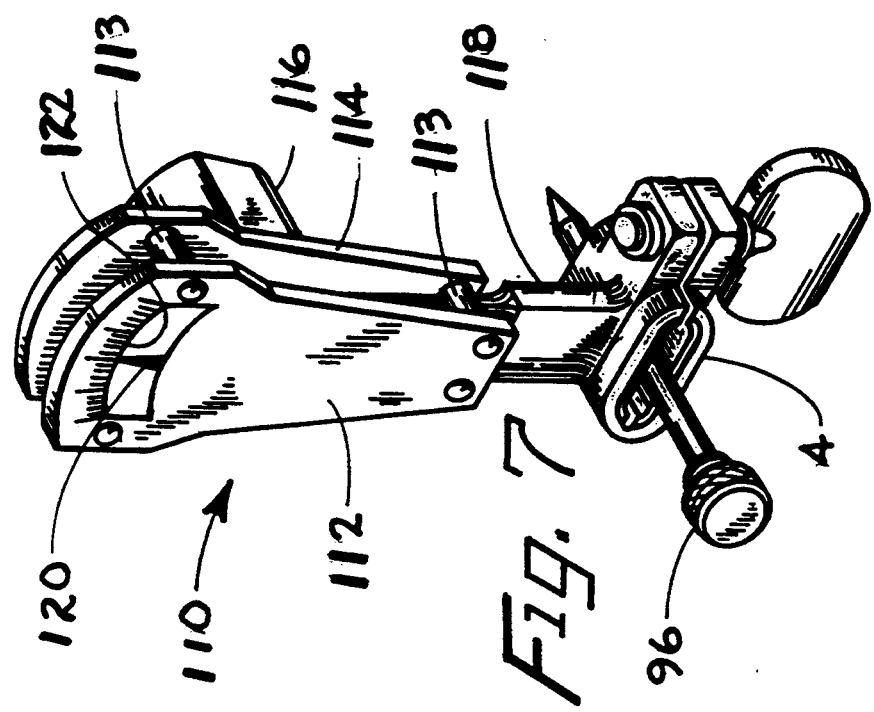
FIG. 7 is a perspective view of the motion indicator of the invention.
Figure 6:
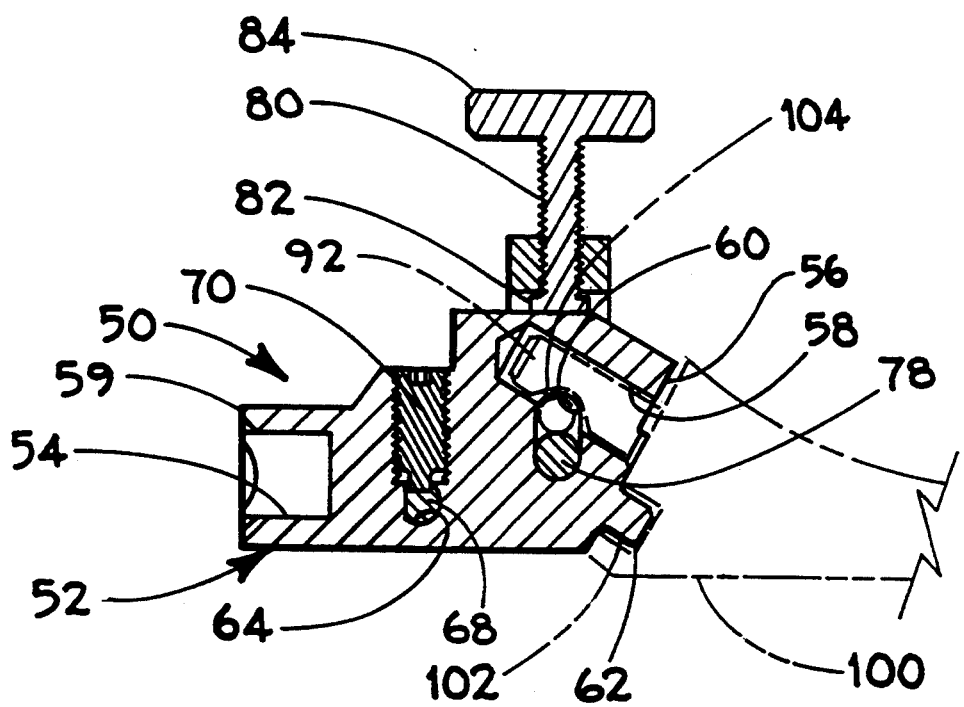
FIG. 6 is a center line sectional view of the adapter of FIG. 5. A portion of a rasp is shown for illustrative purposes.
Figure 5:
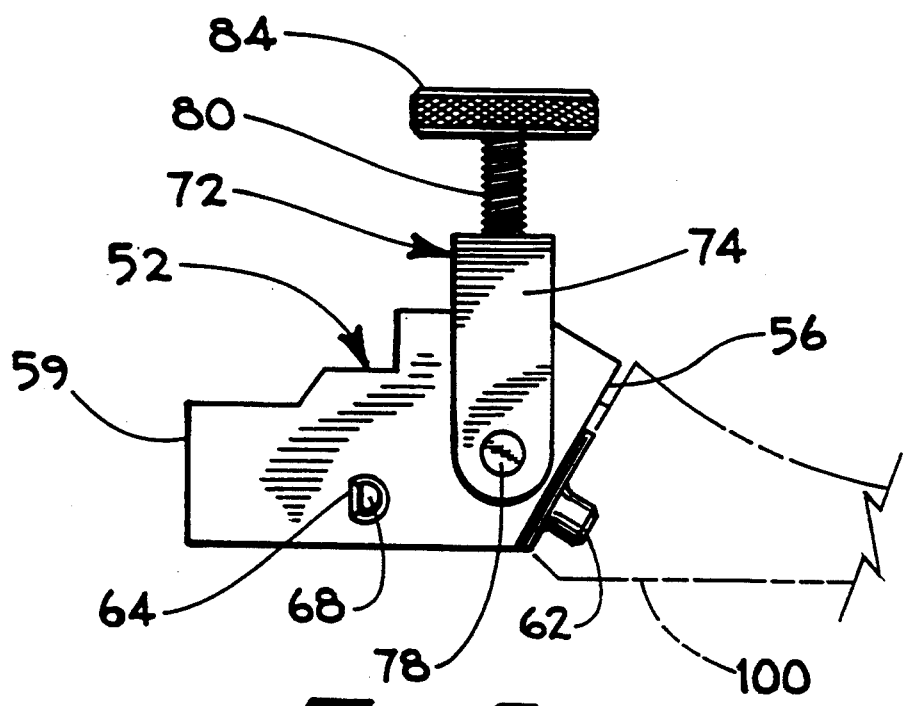
FIG. 5 is a side elevation view of the rasp torque adapter of the invention. A portion of rasp is shown in broken lines for illustrative purposes.
Figure 9:
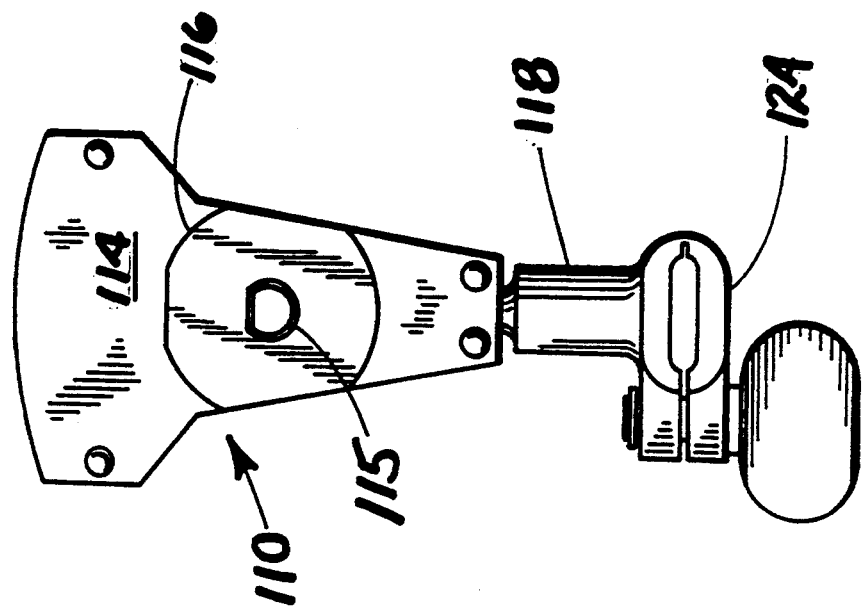
FIG. 9 is a rear elevation view of the motion indicator of the invention of the invention.
Figure 8:
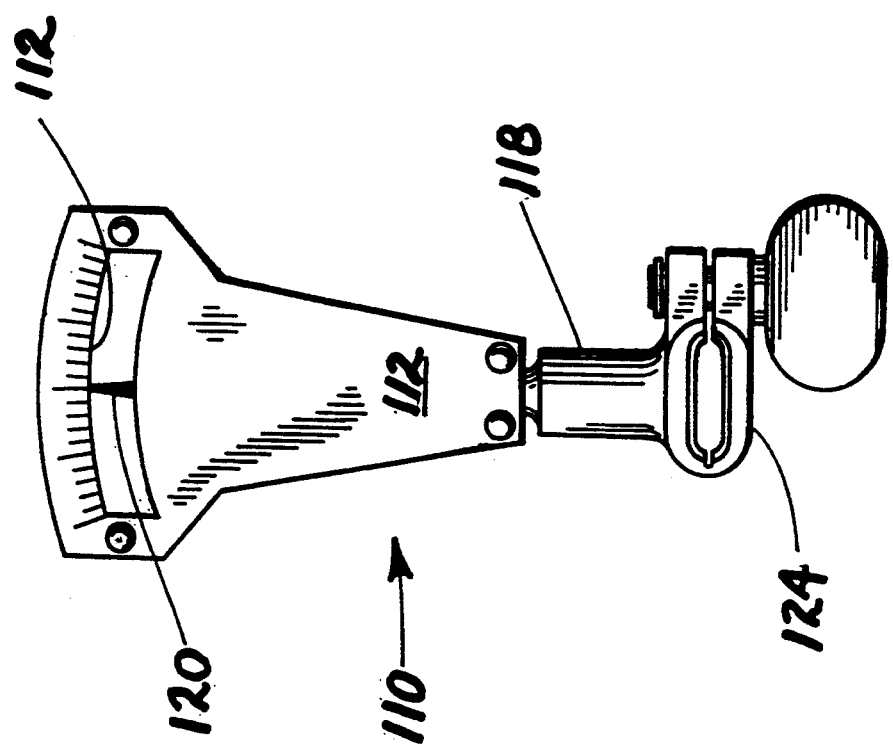
FIG. 8 is a front elevation view of the motion indicator of the invention.
Figure 10:
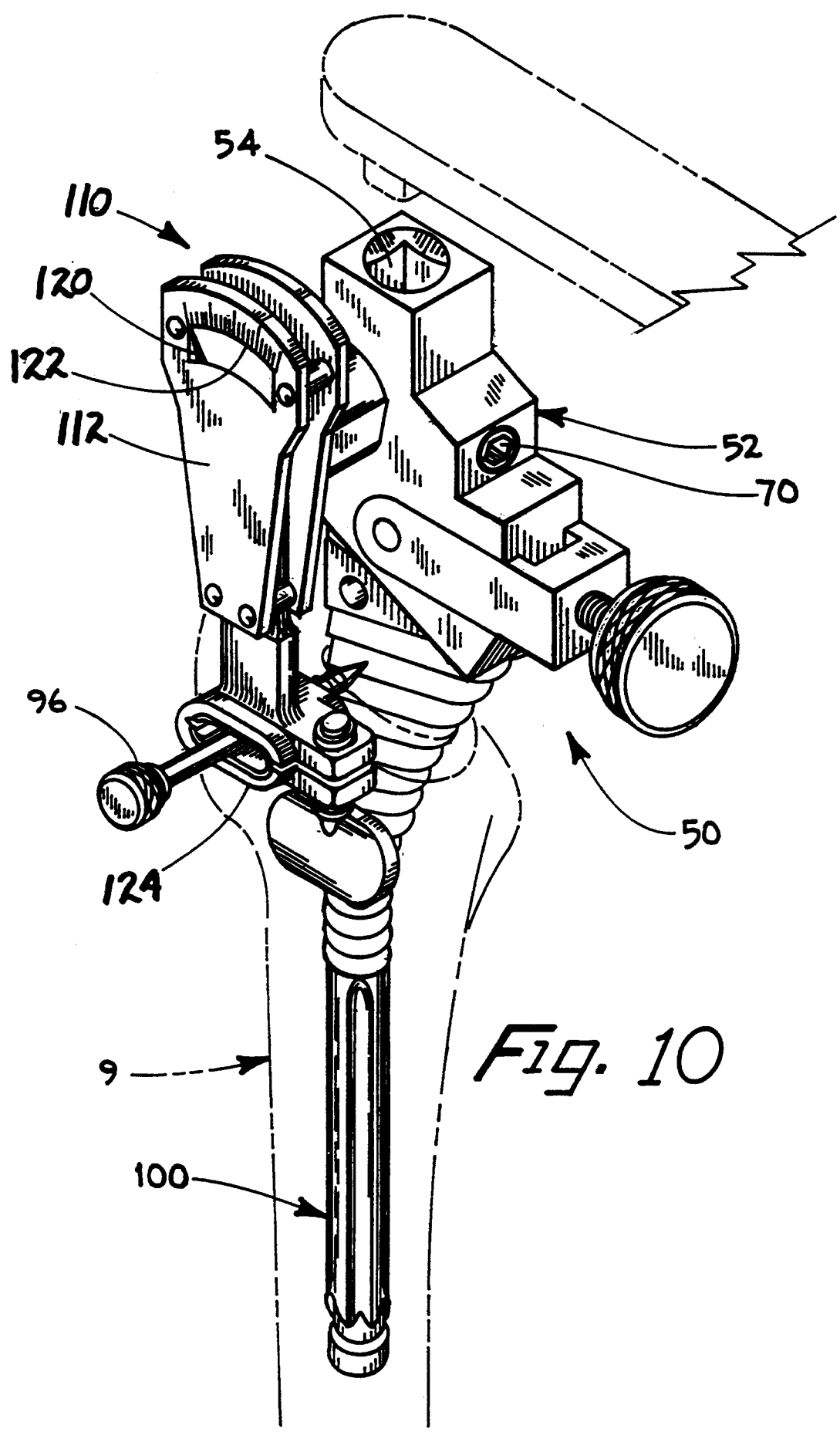
FIG. 10 is a perspective view of the torque adapter secured to a femoral rasp partially seated within the medullary canal of a femur's proximal end (shown in broken lines only)i. A motion indicator is secured to the torque adapter. A torque wrench is partially illustrated in broken lines.

Rasp torque wrench adapter 50 is illustrated in FIGS. 4-6 and includes a housing 52 having an internally squared socket 54 formed in one end thereof. In general, adapter 50 defines a rasp contacting end 56 and a torque wrench adapting end 59. Socket 54 is formed in end 59. A blind bore 58 is formed in housing 52 and extends from end 56 as illustrated in the cross sectional view of FIG. 6. An elongated through bore 60 is formed through housing 52 in communication with blind bore 58. A nipple 62 extends outwardly from end 56 adjacent the opening of blind bore 58. A second through bore 64 is formed through housing 52 generally parallel with throughbore 60 for slidable accommodation of adapter shaft 68. A set screw 70 is threadably accommodated within a threaded blind bore as illustrated for frictional engagement with shaft 68 to lock the shaft in a desired position. A bridal 72 having legs 74 interconnected at their upper end by a cross bar 76 is positioned about housing 52. The lower or distal ends of the legs 74 are interconnected by a rod 78 accommodated within elongated throughbore 60 such that rod 78 is shiftable in a lateral direction within throughbore 60. A threaded shaft 80, having a foot 82 and head 84 is rotatably accommodated within a threaded bore of bridal cross bar 76 such that foot 82 is in contact with housing 52 as shown. As shaft 80 is rotated in one direction bridal 72 is drawn away from housing 52 such that rod 78 is in interference with blind bore 58. As the shaft is rotated in an opposite direction, the bridal is urged toward the housing such that rod 78 is clear from blind bore 58 as is illustrated in FIG. 6.

Motion indicator 110 illustrated in the figures includes a front and back plate 112, 114 held in a spaced apart relationship by a plurality of spacers 113. A connection port 116 extends outwardly from back plate 114 and includes a central blind bore 115. A leg 118 extends downwardly from between the plates and is connected to an internal spring mechanism (not shown). The spring mechanism (not shown) is linked to an indicator needle 120 which is visible through window 122 in front plate 112. A clamp 124 is connected to the leg 118 for clamping engagement with a anchor pin 126. The internal spring mechanism of the motion indicator is known in the art and therefore not illustrated further. It should suffice to say that with the leg 118 secured against movement by clamping to anchor pin 126 (which is driven into a femur) any slight rotation of the motion indicator 110 relative to the femur causes a deflection in indicator needle 120.

In use, after the medullary canal of the femur has been formed by rasping to an extent wherein the surgeon believes the hip stem prosthesis should fit, the rasp 100 is impacted into the prepared medullary canal of the femur and the rasp handle (not shown) is removed. The rasp includes a shaft 92 extending longitudinally from the rasp body and a blind bore 102 adjacent to the shaft. Shaft 92 includes an arcuate notch 104 which is engaged by the rasp handle to grasp the rasp. A nipple from the handle is positioned within the blind bore of the rasp. The construction of the rasp and a discussion of the handle mechanism (not shown) may be had by reference to U.S. patent application Ser. No. 07/455,536, incorporated herein by reference.

Once the rasp is seated within the femur's canal, torque adapter 50 is slid onto the rasp such that the shaft 92 of the rasp is inserted into the blind bore of the adapter 50 and nipple 62 of the adapter is accommodated within blind bore 102 of the rasp body. Shaft 80 of the adapter 50 is rotated to urge bridal 72 away from the adapter until cross bar 78 is firmly seated within notch 104 of the rasp shaft 92. Set screw 70 is loosened such that shaft 68 may be slid until one of its longitudinal ends is generally flush with the side wall of the adapter 50 housing. Shaft 68 is illustrated in FIG. 4 in solid lines in one of its positions and in broken lines in a second position. The particular direction in which the shaft is slid is dependant upon which of the patient's hips is being worked on and which surgical approach is selected. The shaft 68 is slid such that the shaft is fully exposed. Set screw 70 is tightened such that shaft 68 is rigidly secured to housing 52. The surgeon next connects motion indicator 110 onto shaft 68 such that the shaft is accommodated by the blind bore 115 and is secured thereto by a set screw (not shown). Anchor pin 96 is loosely positioned within the clamp of leg 118 and is driven a distance into the femur sufficient to temporarily secure the pin within to the femur. The wing nut of clamp 124 is rotated to cause the clamp to engage the anchor pin and thereby stabilize the leg against movement relative to the femur. A torque wrench 101 (shown in broken lines) is connected to the socket 54 of adapter 50 and torque force is applied to the adapter/rasp combination. If motion is experienced between the adapter/rasp combination and the femur, leg 118 of indicator 110 will rotate slightly with the femur causing indicator needle 120 to deflect away from its central normal position. Measurement indicia on adjacent window 122 provides an indication to the surgeon on the amount of relative movement experienced. The surgeon is therefor given a visible and positive indication of movement, or lack thereof, and the amount of movement at the rasp/femur junction. It is the surgeon's determination if the motion detected is significant requiring additional modification of the medullary canal of the femur. After the surgeon determines the canal to be satisfactorily prepared to accommodate an implant, the rasp is removed and the implant 2 is seated within the canal.

A number of years after the implant has been inserted it is not unusual for a patient to experience pain about the prosthetic joint. It has been determined that the pain may be attributable to a plurality of factors. One of the factors which may cause pain in the joint is micromotion between the implant and bone. If movement occurs between the implant and bone a revision surgery may be required to reshape the medullary canal of the bone and implant a different prosthesis. If motion is not experienced revision may not be necessary. To test the fit of the implant within the canal, the surgeon connects torque wrench adapter 30 to implant 2 by inserting arm 36 into the extraction bore and tightening screw 42. A full and complete description of the connection of adapter 30 to the implant may be had by reference to the incorporated U.S. patent application. After adapter 30 is connected, motion indicator 110 is slid onto arm 44 and connected thereto by a set screw not shown. An anchor pin 96 is again loosely positioned within the clamp of leg 118 and is driven a distance into the femur to temporarily secure the pin to the femur. The wing nut of clamp 124 is rotated to cause the clamp to engage the anchor pin 96 and thereby stabilize the leg 118 of the indicator 110 against movement relative to the femur. A torque wrench (not shown) is connected to the socket 46 of adapter 30 and torque force is applied to the adapter/implant combination. If motion is experienced between the adapter/implant combination and the femur,
leg 118 is caused to rotate with the femur relative to the implant which causes a corresponding deflection in indicator needle 120. Again, the surgeon is given a visible and positive indication of relative movement between the prosthesis and femur when the torque force is applied.

It should be understood that the system and instrumentation of the system described above are not to be limited to the precise forms disclosed, but may be modified within the scope of the appended claims.

We claim:

1. A system for preparing a medullary canal of a bone to accept a prosthetic implant and for torsionally testing a junction between the bone about the prepared medullary canal and a device inserted into said canal and for visually indicating movement between said device inserted into said canal and said canal when said device is torsionally loaded; said system comprising;

a rasp means having a body with a plurality of teeth for scraping engagement with the side walls of said medullary canal to remove a quantity of bone stock from said walls as said rasp means is inserted into said canal, said rasp means further including a handle removably connected to said rasp body;

a rasp adapter connectable to said rasp body and including a shaft extending outwardly from said adapter and a socket for accommodating a drive member of a torquing device;

an indicator means for connection to said shaft of said rasp adapter for indicating relative movement between said bone and the body of said rasp when said rasp is inserted into said intramedullary canal and torque force is applied to said body by a torquing device connected to said rasp adapter at said socket;

a prosthetic implant having a distal portion for seating within said intramedullary canal of the bone and a proximal portion for extending outwardly of said canal when said distal portion is seated within said canal;

an implant adapter connectable to said proximal portion of said implant when said distal portion of said implant is seated within said canal, said implant adapter including a socket accommodating the drive of a torquing device and a shaft for connection of said indicator means;

said indicator means being connectable to said shaft of said implant adapter for indicating relative movement between said implant and said canal when said distal end of said implant is seated within said canal and the torquing device is connected to the socket of said implant adapter and torque force is applied.

2. The system of claim 1 wherein said rasp body includes a rod extending outwardly therefrom for communication with said handle, said rasp adapter including a housing including a handle port with locking means in communication therewith for releasibly securing the rod of said rasp within said port to secure said rasp adapter to said rasp body, said shaft of said rasp adapter being slidable between first and second longitudinal extremes relative to said housing.

3. The system of claim 1 wherein said indicator means includes a housing including an input port, said indicator means and further including a lower depending leg shiftable relative to said housing, an indicator carried by said housing and operatively associated with said leg such that as said leg shifts relative to said housing said indicator deflects away from a normal position, said leg adapted to be anchored at a distal end, said shaft of said rasp adapter and said implant adapter being accommodated within said input port of said housing means.

4. A device connectable to a proximal end of a rasp body for accommodating the drive shaft of a torque device, said rasp including a shaft extending outwardly from the proximal end of said rasp body and a recess formed adjacent said shaft, said device comprising a body having a bore formed therein for accommodating said shaft of said rasp body, a nib extending from said body and being accommodated within said recess, lock means carried by said body for locking said rasp body to said device, a head formed in said body for accommodating said drive shaft, and a connection shaft extending laterally from said body, said connection shaft constituting means for connecting a motion sensor device to said device.

5. The device of claim 4 wherein said lock means includes a channel extending through said body in flow communication with said bore, a bar carried within said channel and shiftable between a first position with said bar in interference with said bore and a second position with said bar clear of said bore, said shaft of said rasp including a notch, said bar being accommodated within said notch of said shaft when said rod is in said first position and said shaft is inserted within said bore.

6. The device of claim 4 wherein said connection shaft is slidably carried by said body and shiftable between first and second longitudinal positions, a lock screw carried by said housing engagable with said connection shaft for securing said connection shaft in one of its said first and second positions.

* * * * *